(12) United States Patent
Paul et al.

(10) Patent No.: US 8,388,681 B2
(45) Date of Patent: Mar. 5, 2013

(54) INTRAOCULAR LENSES HAVING A VISIBLE LIGHT-SELECTIVE-TRANSMISSIVE-REGION

(75) Inventors: Marlene L Paul, Laguna Niguel, CA (US); Michael D Lowery, Irvine, CA (US); Stephen W Laguette, Santa Barbara, CA (US); Mark H Bandhauer, Orange, CA (US)

(73) Assignee: Abbott Medical Optics Inc., Santa Ana, CA (US)

( * ) Notice: Subject to any disclaimer, the term of this patent is extended or adjusted under 35 U.S.C. 154(b) by 0 days.

(21) Appl. No.: 13/243,306

(22) Filed: Sep. 23, 2011

(65) Prior Publication Data

US 2012/0010703 A1   Jan. 12, 2012

Related U.S. Application Data

(62) Division of application No. 11/025,293, filed on Dec. 28, 2004, now Pat. No. 8,043,371.

(60) Provisional application No. 60/533,095, filed on Dec. 29, 2003.

(51) Int. Cl.
 *A61F 2/16* (2006.01)
(52) U.S. Cl. .......................................... 623/6.17; 623/6.6
(58) Field of Classification Search ........................ None
See application file for complete search history.

(56) References Cited

U.S. PATENT DOCUMENTS

| | | | |
|---|---|---|---|
| 4,304,895 A | 12/1981 | Loshaek | |
| 4,390,676 A | 6/1983 | Loshaek | |
| 4,528,311 A | 7/1985 | Beard et al. | |
| 4,617,374 A | 10/1986 | Pruett et al. | |
| 4,636,212 A | 1/1987 | Posin et al. | |
| 4,681,412 A | 7/1987 | Lemelson | |
| 4,716,234 A | 12/1987 | Dunks et al. | |
| 4,737,322 A | 4/1988 | Bruns et al. | |
| 4,753,654 A | 6/1988 | Posin et al. | |
| 4,863,466 A | 9/1989 | Schlegel | |
| 4,929,250 A | 5/1990 | Hung et al. | |
| 4,955,904 A | 9/1990 | Atebara et al. | |
| 4,963,160 A | 10/1990 | Hung et al. | |
| 4,998,817 A | 3/1991 | Zeltzer | |
| 5,008,102 A | 4/1991 | York | |
| 5,047,447 A | 9/1991 | Gallas | |
| 5,098,445 A | 3/1992 | Hung et al. | |
| 5,120,120 A | 6/1992 | Cohen | |
| 5,172,256 A | 12/1992 | Sethofer et al. | |
| 5,235,358 A | 8/1993 | Mutzhas et al. | |
| 5,269,813 A | 12/1993 | Yoshida et al. | |
| 5,272,151 A | 12/1993 | Marzi et al. | |

(Continued)

FOREIGN PATENT DOCUMENTS

| | | |
|---|---|---|
| DE | 3428895 A1 | 2/1986 |
| EP | 161765 B1 | 10/1988 |

(Continued)

OTHER PUBLICATIONS

International Search Report for Application No. PCT/US2004/43627, mailed on Dec. 23, 2005, 5 pages.

(Continued)

*Primary Examiner* — David H Willse
*Assistant Examiner* — Javier Blanco
(74) *Attorney, Agent, or Firm* — Abbott Medical Optics Inc.

(57) ABSTRACT

Intraocular lenses are provided having a visible-light selective transmissive zone defined therein. The visible light-selective transmissive zone can be located near the lens center and designed to reduce the transmission of any wave-length of visible light specifically light in the blue light region having wavelength between approximately 400λ to 550λ. In one embodiment he IOLs are made from acrylates and the light absorbing compound is a yellow dye.

3 Claims, 3 Drawing Sheets

U.S. PATENT DOCUMENTS

| | | | |
|---|---|---|---|
| 5,298,033 | A | 3/1994 | Hung et al. |
| 5,374,663 | A | 12/1994 | Daicho et al. |
| 5,376,650 | A | 12/1994 | Weaver et al. |
| 5,399,692 | A | 3/1995 | Hung et al. |
| 5,470,932 | A | 11/1995 | Jinkerson |
| 5,500,024 | A | 3/1996 | Hung et al. |
| 5,528,322 | A | 6/1996 | Jinkerson |
| 5,534,041 | A | 7/1996 | Havens et al. |
| 5,543,504 | A | 8/1996 | Jinkerson |
| 5,657,726 | A | 8/1997 | Diggs |
| 5,662,707 | A | 9/1997 | Jinkerson |
| 5,846,457 | A | 12/1998 | Hoffman |
| 5,866,635 | A | 2/1999 | Collins et al. |
| 5,922,246 | A | 7/1999 | Matsushita et al. |
| 6,143,028 | A | 11/2000 | Galin et al. |
| 6,158,862 | A | 12/2000 | Patel et al. |
| 6,187,042 | B1 | 2/2001 | Sheets, Jr. et al. |
| 6,224,210 | B1 | 5/2001 | Chateau et al. |
| 6,242,551 | B1 | 6/2001 | Tsuzuki et al. |
| 6,244,707 | B1 | 6/2001 | Faubl |
| 6,277,940 | B1 | 8/2001 | Niwa et al. |
| 6,280,471 | B1 | 8/2001 | Peyman et al. |
| 6,305,801 | B1 | 10/2001 | Kerns, Jr. et al. |
| 6,310,215 | B1 | 10/2001 | Iwamoto |
| 6,326,448 | B1 | 12/2001 | Ojio et al. |
| 6,387,127 | B1 | 5/2002 | Muller-Lierheim |
| 6,399,805 | B2 | 6/2002 | Wolf et al. |
| 6,432,137 | B1 | 8/2002 | Nanushyan et al. |
| 6,604,824 | B2 | 8/2003 | Larson |
| 7,098,283 | B2 | 8/2006 | Lai |
| 7,232,896 | B2 | 6/2007 | Miki et al. |
| 7,241,312 | B2 | 7/2007 | Lai et al. |
| 7,278,737 | B2 | 10/2007 | Mainster et al. |
| 7,677,725 | B2 | 3/2010 | Piers et al. |
| 2002/0042653 | A1 | 4/2002 | Copeland et al. |
| 2002/0082312 | A1 | 6/2002 | Lai |
| 2003/0078359 | A1 | 4/2003 | Ichinohe |
| 2003/0144733 | A1 | 7/2003 | Brady et al. |
| 2006/0115516 | A1 | 6/2006 | Pearson et al. |

FOREIGN PATENT DOCUMENTS

| | | | |
|---|---|---|---|
| EP | 485197 | A1 | 5/1992 |
| EP | 488145 | A2 | 6/1992 |
| EP | 359829 | B1 | 11/1993 |
| EP | 1043365 | A1 | 10/2000 |
| EP | 1030194 | B1 | 12/2002 |
| EP | 1293541 | A2 | 3/2003 |
| FR | 2622984 | A1 | 5/1989 |
| JP | 1501172 | T | 4/1989 |
| JP | 1204668 | A | 8/1989 |
| JP | 402273714 | | 11/1990 |
| JP | 6072151 | A | 3/1994 |
| JP | 6258604 | A | 9/1994 |
| JP | 6262861 | A | 9/1994 |
| JP | 6324293 | A | 11/1994 |
| JP | 7024052 | A | 1/1995 |
| JP | 7258166 | A2 | 10/1995 |
| JP | 8503997 | T | 4/1996 |
| JP | 9187500 | | 7/1997 |
| JP | 10111641 | A | 4/1998 |
| JP | 10195324 | A | 7/1998 |
| JP | 411253480 | | 9/1999 |
| JP | 2003144538 | A | 5/2003 |
| JP | 2003144638 | A | 5/2003 |
| WO | WO8705712 | A1 | 9/1987 |
| WO | WO8802871 | A1 | 4/1988 |
| WO | WO8907952 | A1 | 9/1989 |
| WO | WO9511279 | A1 | 4/1995 |
| WO | WO9825173 | A1 | 6/1998 |
| WO | WO9825180 | A1 | 6/1998 |
| WO | WO9844380 | A1 | 10/1998 |

OTHER PUBLICATIONS

International Search Report for Application No. PCT/US2005/14465, mailed on Aug. 31, 2005, 4 pages.

| Step | Process Description | Top View | Side View |
|---|---|---|---|
| Step 1 2A | Acrylic Button | | |
| Step 2 2B | Drill Central 2-4 mm Leaving the Bottom Closed | | |
| Step 3 2C | Fill Button w/ Dye Containing Acrylic Material | | |
| Step 4 2D | Lathe Excess Material | | |
| Step 5 2E | Fill Button with Clear Acrylic to Encapsulate Yellow Zone | | |
| Step 6 | Lathe/Mill to form IOL | | |

FIG. 2

INTRAOCULAR LENSES HAVING A VISIBLE LIGHT-SELECTIVE-TRANSMISSIVE-REGION

RELATED APPLICATIONS

This application is a divisional application of, and claims priority to, U.S. patent application Ser. No. 11/025,293 filed Dec. 28, 2004, now U.S. Pat. No. 8,043,371 issued on Oct. 25, 2011, which claims the benefit of U.S. provisional application No. 60/533,095 filed Dec. 29, 2003, the entire contents of each of which are hereby incorporated by reference in their entirety for all purposes as if fully set forth herein.

FIELD OF THE INVENTION

The present invention relates to intraocular lenses (IOL) suitable for implantation into mammals. More specifically, the present invention relates to intraocular lenses having a region defined therein that contains at least one light absorbing dye, a surface coating or other means for creating a visible light-selective-transmissive region in the IOL.

BACKGROUND OF THE INVENTION

There are three primary structures within the human eye that are essential to vision and subject to age-related damage: the lens (100), cornea (102) and retina (104) (see FIG. 1). The retina is a multi-layered sensory tissue that lines the back of the eye. It contains millions of photoreceptors that capture light rays and convert them into electrical impulses. These impulses travel along the optic nerve (106) to the brain where they are turned into images. There are two types of photoreceptors in the retina: rods and cones. The retina contains approximately 6 million cones. The cones are contained in the macula, the portion of the retina responsible for central vision. They are most densely packed within the fovea, the very center portion of the macula, Cones function best in bright light and allow us to appreciate color. There are approximately 125 million rods. They are spread throughout the peripheral retina and function best in dim lighting. The rods are responsible for peripheral and night vision. The retina is essential for vision and is easily damaged by prolonged unprotected exposure to visible and near visible light. Light-induced retinal pathologies include cystoid macular oedema, solar retinopathy, ocular melanomas and age-related macular degeneration (ARMD). Light-induced retinal damage is classified as structural, thermal or photochemical and is largely determined by the exposure time, power level and wavelength of light (W. T. Ham. 1983. Journal of Occupational Medicine. 25:2 101-102).

In healthy adults the retina is generally protected form the most severe forms of light-induced damage by the outer eye structures including the cornea and crystalline lens. The cornea is a transparent proteinaceous ocular tissue located before the iris and is the only eye structure exposed directly to the environment. The cornea is essential for protecting the delicate internal structures from damage and facilites the transmission of light through the aqueous media to the crystalline lens. The cornea is the primary light filter and therefore is particularly susceptible to excessive light exposure-related damage including cornea-conjunctival diseases such as pterygium, droplet climatic keratopathy, and pinguecula. In the healthy eye the cornea, in conjunction with the aqueous medium, absorbs, or blocks, wavelengths ($\lambda$ shall be used hereinafter to denote wavelengths of light in nanometers) in the short ultraviolet (UV)-B and UV-C region (less than ~$320\lambda$).

The crystalline lens is an accommodating biological lens lying directly behind the iris and cornea and facilitates the convergence of both far and near images onto the retina. The natural crystalline lens blocks near UV radiation (UV-A) ($320\lambda$, to $400\lambda$) from reaching the retina. Therefore, most of the damaging UV A, B and C radiation are prevented from reaching the retina in healthy people with an intact crystalline lens and cornea. Thus in the normal mammalian eye only wavelengths between $400\lambda$-$1,400\lambda$ can reach the retina. However, high transmittance levels of violet-to-blue light (wavelengths from about $400\lambda$ to about $515\lambda$) has been linked to retinal damage, macular degeneration, retinitis pigmentosa, and night blindness. In addition, blue light tends to be scattered in the atmosphere, especially in haze, fog, rain, and snow, which in part can cause glare, and diminished visual acuity. As the eye ages the crystalline lens begins to take on a yellow tint that does not adversely affect visual acuity but does absorb the majority of near UV radiation. Thus, the natural crystalline lens protects the eye's delicate retina from near UV light throughout life and subtly yellows with age increasing the about of shorter wavelength blue light that is absorbed.

The natural crystalline lens is also susceptible to age-related degenerative eye diseases such as cataracts. Cataract is a clouding of the crystalline lens caused by the coagulation of lens proteins within the capsular sac. Many ophthalmologists believe that cataract formation results from a life time of oxidative insults to the lens and is exacerbated by smoking, excessive exposure to bright light, obesity and diabetes. Cataracts develop slowly in most people and eventually reach the point where vision is substantially impaired resulting in near to total blindness. In these persons lens removal and replacement with synthetic polymer intraocular lenses (IOLs) is the preferred means for restoring normal sight. However, once the natural crystalline lens is removed the retina is left unprotected from damaging UV and short wavelength blue light. Thus early synthetic IOLs were provided with UV absorbing compounds such as benzophenone and benzotriazole-based UV light absorbers. Intraocular lenses provided with UV absorbing compounds soon became common-place and are found in virtually all IOLs. Moreover, many benzophenones and benzotriazoles are polymerizable and thus can be stably integrated into most modern IOL compositions including acrylates, silicones, and hydrophilic hydrogel comonomers and copolymers.

Recently, blue light absorbing dyes have been incorporated into IOL materials in order to approximate the blue light blocking effects of the aging adult natural crytalilline lens. Many IOL manufactures are designing lenses that contain yellow dyes at concentrations that absorb, or block visible light in the blue region. For example, U.S. Pat. No. 4,390,676, describes polymethylmethacrylate (PMMA) polymer IOLs incorporating yellow dyes that selectively absorb UV/blue light radiation up to approximately $450\lambda$. U.S. Pat. Nos. 5,528,322; 5,543,504; and 5,662,707 are assigned to Alcon and disclose acrylic-functionalized yellow azo dyes having an inert chemical spacer between the dye and acrylic portions of the molecule. Thus the blue light-absorbing portion of the molecule is protected from undesirable color shifts when polymerized with the lens polymer. Moreover, because the dye is acrylic-functionalize it is polymerizable with the lens polymer and thus stably incorporated into the IOL polymer matrix. Similarly, Menicon holds U.S. Pat. Nos. 6,277,940 and 6,326,448 both disclosing specific acrylic-modified azo dyes structurally similar to Alcon's. Hoya owns U.S. Pat. No. 5,374,663 that discloses non-covalently linked yellow dyes including solvent yellow numbers 16, 29 and others incorporated into a PMMA matrix. Moreover, Hoya also owns U.S. Pat. No. 6,310,215 that discloses acrylic-functionalized pyrazolone dyes suitable for use in acrylic and silicone IOLs.

However, these and other prior art IOLs have the blue blocking dyes evenly distributed throughout the IOL material at concentrations that simulate the natural yellow color of the 53 year-old individual's crystalline lens. However, unlike the natural crystalline lens, an IOL is lathed and shaped to a specific diopter power causing the IOL to have a non-uniform thickness. Thus the effective amount of blue light blocking dye is a function of the IOL thickness. Because lens thickness varies with lens shape and diopter power, the effective amount of blue light blocking compound at any one point on the IOL varies. This is especially relevant near the lens center where the constricted pupil concentrates and focuses the light in bright light conditions. Moreover, the entire lens contains dye including its surfaces and thus eye's delicate tissues are in intimate contact with the dye. Consequently, patients that are sensitive to blue blocking dyes cannot benefit from blue light blocking lenses containing those dyes. Furthermore, some patients may develop hypersensitivity to the blue blocking dye after prolonged contact.

As stated previously, the prior art IOLs, like the natural aging lens, have a yellow pigment distributed throughout the entire lens. Consequently, all light and images are filtered through a yellow color before being projected on the retina. For many applications this is desirable, for instance people who engage in certain outdoor sports or activities including skiers, baseball players, football players, pilots, and boaters are exposed to high levels of ultraviolet, blue, and visible light radiation which can affect visual acuity required in such activities. Drivers of motor vehicles also have specific needs in terms of reducing glare and enhancing visual acuity under bright, sunlit driving conditions and reducing headlight glare at night. For these specific needs, alteration of light transmittance over the spectrum of visible light including the blue-violet end of the visible spectrum to the red end of the spectrum may be necessary. However, there are non-vision related eye functions that are impaired when the inner eye is continuously shielded from blue light wave-lengths such as those associated with circadian rhythm and melatonin secretion.

Therefore, it is an objective of the present invention to provide an IOL having a uniform distribution of blue light blocking compound that does not vary with lens diopter.

It is another objective of the present invention to provide an IOL having one or more blue light blocking compounds that is not in intimate contact with delicate eye structures.

It is yet another objective of the present invention to provide an IOL having blue light blocking properties limited to a defined region of the lens to minimize interference with non-vision related eye function and yet maximize the blue light blocking properties under bright light conditions.

SUMMARY OF THE INVENTION

The present invention achieves these and other objectives by providing an intraocular lens (IOL) having a blue light (visible light) blocking region localized to the central portion of the IOL rather than dispersed throughout and wherein the blue light blocking region is encased in non-blue blocking compound-containing polymer.

The present invention is an intraocular IOL suitable for implantation into the eye of a mammal wherein the lens comprises a visible light selective-transmissive-region, and wherein the visible light-selective-transmissive region is less than the entire IOL. In one embodiment of the present invention the IOL has a defined region that comprises at least one light absorbing dye, specifically dyes that absorb visible light in the wavelengths between approximately 400 and 550 nanometers (nm).

The IOLs of the present invention may be composed of any biocompatible polymer suitable for use in forming an intraocular lens. For example, but not limited to poly(methylmethacrylate) (PMMA). Additional polymers may be used when made using monomers selected from the non-limiting group consisting of phenylethylacrylate (PEA), phenylethylmethacrylate (PEMA), methylphenylacrylates, methylphenylmethacrylates, 2-hydroxyethyl methacrylate (HEMA). Moreover, heterocyclic N-vinyl compounds containing a carbonyl functionality adjacent to the nitrogen in the ring, and particular N-vinyl lactams such as N-vinyl pryrolidone are also suitable for use in accordance with the teachings of the present invention. Moreover, the IOLs of the present invention may also be cross-linked using di- or multi-functional monomers and in small amounts as is well known in the art. Representative crosslinking agents include ethylene glycol dimethacrylate, triethylene glycol dimethacrylate and trimethylolpropane trimethacrylate. The cross linking agents are typically dimethacrylates or diacrylates, although dimethacrylamides are also known.

The light absorbing dye used to form the visible light selective transmissive-region can be any dye capable of absorbing light of predetermined wavelengths within the visible light spectrum. Exemplary light absorbing dyes include, but not limited to polymerizable yellow dyes based on the azo dye system that contain polymerizable acrylate/methacrylate groups such as those disclosed in U.S. Pat. No. 5,662,707, the entire contents of which is hereby incorporated herein by reference, specifically column 4 beginning at line 43 through column 10 line 3. Other suitable yellow dues include, without limitation, methine dyes, benzene sulfonic acid, 4-(4,5-dihydro-4-((2-methoxy-5-methyl-4-((2-(sulfooxy)ethyl)sulfonyl)phenyl)azo-3-methyl-5-oxo-1H-pyrazol-1-yl); [2-naphthalenesulfonic acid, 7-(acetylamino)-4-hydroxyl-3-((4-((sulfooxyethyl)sulfonyl)phenyl)azo)-]; [5-((4,6-dichloro-1,3,5-triazin-2-yl)amino-4-hydroxy-3-((1-sulfo-2-naphthalenyl)azo-2, 7-naphthalene-disulfonic acid, trisodium salt]; [copper, 29H, 31H-phthalocyaninato(2-)-$N_{29}$, $N_{30}$, $N_{31}$, $N_{32}$)-, sulfo((4((2-sulfooxy)ethyl)sulfonyl)phenyl)amino)sulfonyl derivative]; and [2,7-naphthalenesulfonic acid, 4-amino-5-hydroxy-3,6-bis((4-((2-(sulfooxy)ethyl)sulfonyl)phenyl)azo)-tetrasodium salt] and others. Theses dyes are particularly beneficial because they are reactive dyes that can be chemically bonded to the IOL polymer so that the lens is colorfast and the dye is non-extractable (i.e. will not bleed or leach out of the lens). However, it is not essential that the dye be polymerizable or capable of bonding to the IOL polymer for example, Solvent Yellow dyes may also be used in accordance with the teachings of the present invention as may any dye capable of absorbing the desired wavelength of light, The IOLs of the present invention are made such that the light absorbing dye is localized to a specific part of the lens, preferably the center portion. This particular configuration has at least two advantages. Ordinarily as light intensity increases the pupil contracts to moderate the amount of light entering the eye and contacting the retina. Thus, in bright light environments the light absorbing region of the present IOL will cover the entire contracted pupil. Conversely, in less intense lighting conditions the dilated pupil will be only partially covered by the light absorbing dye region allowing a fuller spectrum of light to reach the retina. Thus, the present invention provides an IOL that affords the retina maximum protection in high intensity lighting conditions when protection is needed most, while permitting a fuller spectrum of light to reach the retina in subdued, or low light conditions thus enhancing color perception.

In another embodiment of the present invention the light absorbing dye is isolated within the IOL interior such that the dye itself does not contact either the eye's anatomical structures or physiological fluids. This embodiment reduces the possibility of hypersensitivity associated with long term expose to organic dyes and permits a wider range of dyes to be used.

The IOLs of the present invention are fabricated using a manufacturing protocol developed for the present invention and as such represents a related novel invention useful for forming the present IOLs. In one embodiment a polymer disc or "button" is formed having a well formed therein. In another embodiment the well is drilled into the polymer button in a second step. In embodiment the well thus formed is subsequently filled with a similar or identical polymer used to form the IOL; however, a visible light absorbing dye has been added to the polymer and mixed before filling the well. After the well has been filled the lens may be lathe to remove excess dye-containing polymer. Once excess polymer and dye have been removed a final polymer coating is applied to the dye containing IOL. The dye is thus sealed within the IOL's interior. Finally the lens is shaped to form an IOL having predetermined diopter strengths.

One surprising advantage of the present manufacturing process is that IOLs made accordance with the teaching of the present invention have a uniform light absorbing property regardless of diopter strength. Lenses diopter is adjusted by altering the lens dimensions; lens thickness is the most commonly altered dimension when shaping a lens to achieve a desired vision correction. Thus, when the light absorbing dye is homogeneously distributed throughout the structural polymer the amount of light absorbing dye, and hence light absorbing properties of the lens, varies proportionally to lens thickness. Consequently, lenses thus formed do not offer all recipients the same level of protection throughout the full range of available diopter strengths. The manufacturing method of the present invention obviates this problem by isolating the dye within the lens interior and not dispersed homogeneously throughout. Consequently, when the lens is shaped, only non-dye-containing structural polymer is removed and the light absorbing region remains consistent diopter to diopter.

In another embodiment of the present invention the blue-light blocking capacity of the IOL made in accordance with the teachings of the present invention is achieved using a surface treatment. The surface treatment may be of polymer impregnated with at least one dye or use of at least one dye alone. Another type of surface coating is a thin reflective coating. The surface treatment may comprise at least one coating of a comparable material with a slightly different refractive index that allows destructive interference of the desired wavelength. This surface treatment may be applied using molding, spin casting, etching, chemical deposition, vapor deposition, or other suitable technologies.

In another embodiment, diffractive technology may be applied in the optical design to defocus or change the intensity of light transmitted, reducing substantially the amount of the blue light directed in the retinal region of interest.

Other embodiments of the present invention include lenses having additional light absorbing dyes, specifically dyes that absorb light in the ultraviolet region, for example, but not limited to benzophenones and benzotriazoles.

In yet another embodiment of the present invention the IOL is a multi-focal lens with different zones correcting for different vision distances. Selective light transmission may be applied to one or more of these zones to provide for maximal retinal protection in bright light and maximal light transmission or focusing in low light. For multifocal lenses, selective light transmission or selective light focusing may be also used to optimize visual acuity in both bright and low light while reducing glare and halos associated with multifocal lenses. It is understood that the different zones may have the same or different levels of selective light transmission or selective light focusing.

BRIEF DESCRIPTION OF THE FIGURES

FIG. 2 depicts a step-wise manufacturing protocol useful in accordance with the teachings of the present invention.
FIG. 2A depicts forming an acrylic button.
FIG. 2B depicts forming a 2-4 mm well in the button center.
FIG. 2C depicts filling the well thus formed in FIG. 1B with a dye-containing acrylic material.
FIG. 2O depicts lathing the filled button to remove excess dye-containing acrylic material.
FIG. 2E depicts encasing the dye-containing acrylic material with a clear les-grade acrylic.

DEFINITION OF TERMS

"Blue blocker" As used herein "blue blocker" refers to any means that absorbs, reflects, or otherwise interferes with the transmission of light in the electromagnetic spectrum between the wavelengths of 400 nm to 550 nm. Non limiting examples of "blue blocker" includes dyes, surface coatings and surface treatments "Diopter:" A unit of measurement of the refractive power of lenses equal to the reciprocal of the focal length measured in meters.

"Visible light-selective-transmissive-region" As used herein "visible light selective-transmissive-region" shall mean a portion of an intraocular lens (IOL) (mono- or multi-focal) having at least one region of the lens, but less than the whole lens, that reduces the amount of light in the visible region of the electromagnetic region (400 nm-700 nm) that reaches the retina. This may be accomplished using light absorbing dyes, coatings, diffractive patterns or other means, including combinations thereof.

DESCRIPTION OF THE INVENTION

Figure 1:
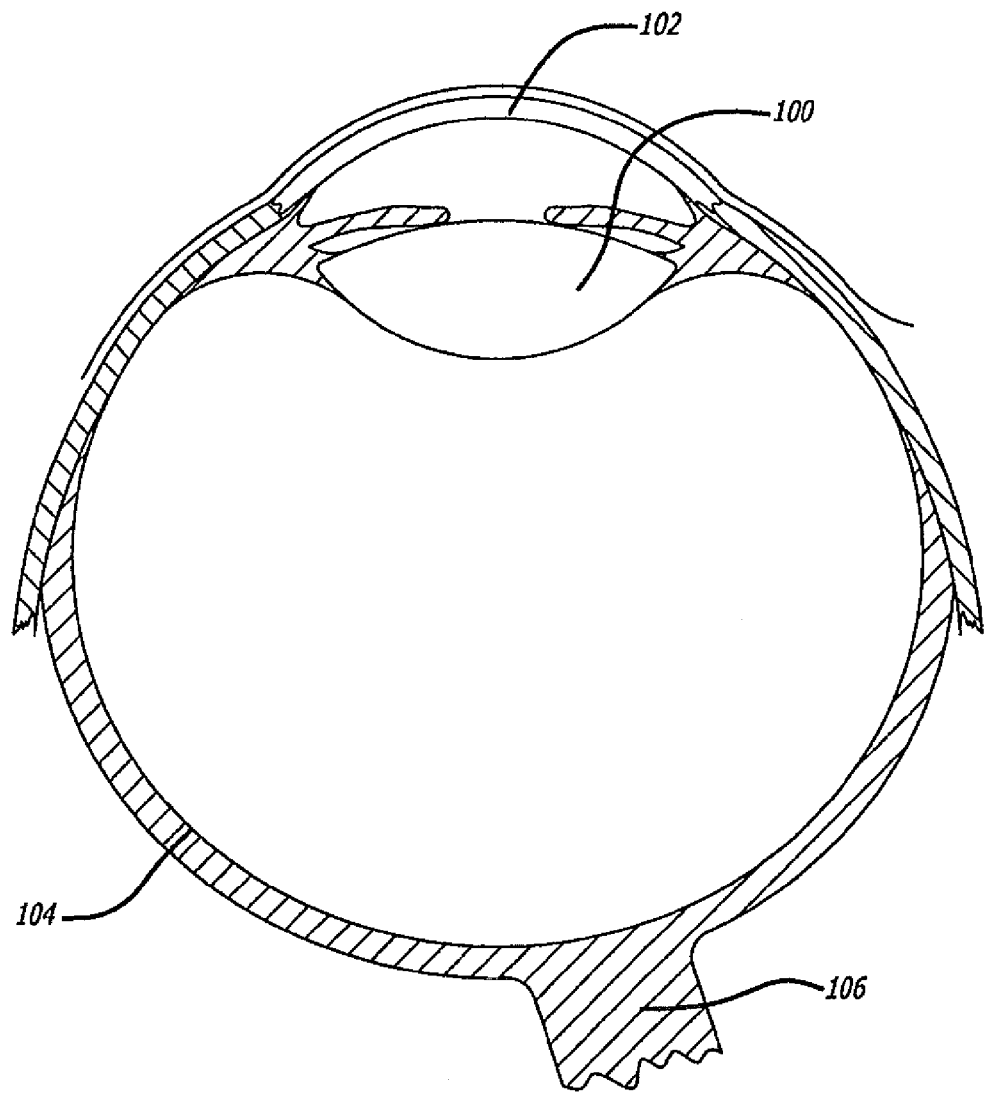
FIG. 1 depicts a cut-away diagram of the human eye.
Figure 3A:
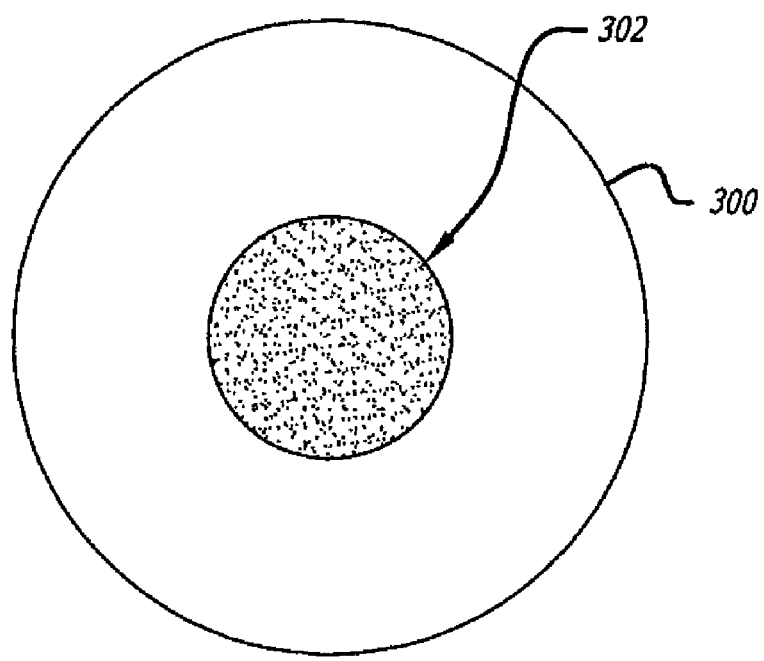
FIG. 3A depicts a mono-focal IOL made in accordance with the teachings of the present invention wherein the IOL is provided with an inner blue-light blocking zone.

The present invention comprises an intraocular lens having a defined visible light-selective-transmissive region. In one embodiment of the present invention visible light selective-transmission region comprises at least one dye that absorbs electromagnetic radiation between the wavelengths of 400 nm to 550 nm ("blue blocker"). In this embodiment central portion of the lens contains a blue blocker while the lens periphery does not (FIG. 3A). The blue blocker may be intrinsic in the material or applied to the lens surface. In bright light the pupil is contracted so that blue blocker can offer potential rentinal protection. In lower lighter, the pupil is dilated and all available light can pass through the periphery. In lower light, retinal protection is not as critical. The blue blocker could be maintained within for example the central portion of the lens, i.e. the central 2 to 4.5 mm, while the lens periphery, i.e. an annular portion from 2.01 mm to 6 mm or 4.5 to 6.5 mm would not contain the blue blocker. A difference in color perception between the two zones in low light may occur. This effect could be minimal as the majority of the color receptors are in the central retinal area (blue blocking portion of the lens) while the retina periphery is better at determining saturation or "shades of gray" (non-blue blocking lens portion).

The light absorbing dye used to form the visible light selective transmissive-region can be any dye capable of absorbing light of predetermined wavelengths within the visible light spectrum. Exemplary light absorbing dyes include, but not limited to polymerizable yellow dyes based on the azo dye system that contain polymerizable acrylate/methacrylate groups such as those disclosed in U.S. Pat. No. 5,662,707, the entire contents of which is hereby incorporated herein by reference, specifically column 4 beginning at line 43 through column 10 line 3. Other suitable yellow dues include, without limitation, methine dyes, benzene sulfonic acid, 4-(4,5-dihydro-4-((2-methoxy-5-methyl-4-((2-(sulfooxy)ethyl)sulfonyl)phenyl)azo-3-methyl-5-oxo-1H-pyrazol-1-yl); [2-naphthalenesulfonic acid, 7-(acetylamino)-4-hydroxyl-3-((4-((sulfooxyethyl)sulfonyl)phenyl)azo)-]; [5-((4,6-dichloro-1,3,5-triazin-2-yl)amino-4-hydroxy-3-((1-sulfo-2-naphthalenyl)azo-2, 7-naphthalene-disulfonic acid, trisodium salt]; [copper, 29H, 31H-phthalocyaninato(2-)-$N_{29}$, $N_{30}$, $N_{31}$, $N_{32}$)-, sulfo((4((2-sulfooxy)ethyl)sulfonyl)phenyl)amino)sulfonyl derivative]; and [2,7-naphthalenesulfonic acid, 4-amino-5-hydroxy-3,6-bis((4-((2-(sulfooxy) ethyl)sulfonyl)phenyl)azo)-tetrasodium salt] and others. Theses dyes are particularly beneficial because they are reactive dyes that can be chemically bonded to the IOL polymer so that the lens is colorfast and the dye is non-extractable (i.e. will not bleed or leach out of the lens). However, it is not essential that the dye be polymerizable or capable of bonding to the IOL polymer for example, Solvent Yellow dyes may also be used in accordance with the teachings of the present invention as may any dye capable of absorbing the desired wavelength of light.

In a preferred embodiment of the present invention a yellow dye available from Eastman Chemicals designated Yellow 035 MA1 and having the structure of Formula 1 is used as the blue light absorbing dye.

Formula 1

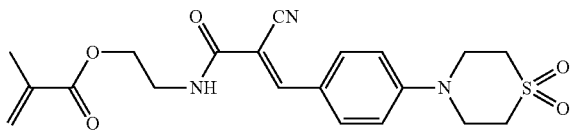

The IOLs of the present invention are made from biocompatible polymers and include, without limitation poly(methylmethacrylate) (PMMA). Additional polymers may be used when made using monomers selected from the non-limiting group consisting of phenylethylacrylate (PEA), phenylethylmethacrylate (PEMA), methylphenylacrylates, methylphenylmethacrylates, 2-hydroxyethyl methacrylate (HEMA). Moreover, heterocyclic N-vinyl compounds containing a carbonyl functionality adjacent to the nitrogen in the ring, and particular N-vinyl lactams such as N-vinyl pyrrolidinone are also suitable for use in accordance with the teachings of the present invention. Furthermore, silicone IOLs and acrylate-silicone hybrid IOLs are considered within the scope of the present invention. Moreover, the IOLs of the present invention may also be cross-linked using di- or multi-functional monomers and in small amounts as is well known in the art. Representative crosslinking agents include ethylene glycol dimethacrylate, triethylene glycol dimethacrylate and trimethylolpropane trimethacrylate. The cross linking agents are typically dimethacrylates or diacrylates, although dimethacrylamides are also known. Additional suitable lens-forming monomers for use in the present invention include listed at column 7, line 63 through column 8 line 40 of U.S. Pat. No. 5,662,707 the contents of which is herein incorporated by reference. See also U.S. Pat. No. 5,269,813 column 2 line 14 through column 7 line 52, specifically Table 1, this U.S. patent is also incorporated by reference both in its entirety and as specifically cited.

The IOLs of the present invention may also contain at least one near ultraviolet (UV) light absorbing compound such as benzophenones and benzotriazoles. Suitable examples can be found in U.S. Pat. Nos. 4,716,234 (specifically see column 3 line 67 through column 10 line 24); 4,963,160 (specifically column 2 line 61 through column 4 line 19); 5,657,726 (specifically column 2 line 36 through column 4 line 67) and 6,244,707 (specifically column 3 line 50 through column 6 line 37) the entire contents of which, specifically the cited columns numbers and lines, are herein incorporated by reference.

In one exemplary embodiment, and not intended as a limitation, the IOL of present invention is a hard IOL comprising PMMA having at least one UV absorbing compound incorporated therein in a UV light absorbing effective amount. However, it is understood that while the present invention will be described using a hard PMMA IOL as an example, it is not limited to hard PMMA IOLs. For example, the present invention is equally suitable for silicone IOLs, acrylic-silicone hybrid IOLs and soft acrylic IOLs. Persons skilled in the art will readily understand the easily adapt the present teachings for use with other IOL structural polymers.

A UV light absorbing effective amount is defined herein as that concentration of UV absorber, or UV absorbers that blocks at least 50% of ambient near UV light from reaching the retina. In one embodiment of the present invention the UV light absorbing compound may be present in the final polymer mixture in the range of between approximately 0.01 weight percent to 5.0 weight percent. The PMMA IOL of the present invention also has a visible-light-selective transmissive zone incorporated near the IOL center having therein a blue light blocking effective amount of at least one yellow dye. A blue light blocking effective amount is defined herein as that concentration of blue light blocking compound, or blue light absorbers that blocks at least 50% of ambient near blue light from reaching the retina. In one embodiment of the present invention the blue light blocking compound may be present in the final polymer mixture in the range of between approximately 0.01 weight percent to 5.0 weight percent (wt. %). In one exemplary embodiment the UV absorbing compound is 0.75 wt. % 2,2',4,4'-tetrahydroxybenzophenone and 0.25% 4-[(2,4-dimethylphenyl)azo]-2,4-dihydro-5-methyl-2-phenyl-3H-pyrozol-3-one.

Turning now to FIG. 2A, an acrylic button, or disc, shaped generally like an IOL is formed from PMMA or other suitable lens grade polymer. Both methods of forming a specific shape and compounding a suitable lens-grade polymer are well known in the art. In one embodiment of the present invention the lens is made from at least 25 wt % to 70 wt. % PMMA. FIG. 2B depicts forming a well in the polymer IOL. The well can be cast into the lens when originally made, or it can be formed into the lens using milling or drilling techniques or other methods known to those skilled in the art. In FIG. 2C a dye-containing lens-grade polymer, generally the same polymer used to form the lens in FIG. 2A, but not limited to that polymer, is added to the well formed in FIG. 2B. The dye is a blue-light absorbing dye, generally a yellow dye, is present in the lens-grade polymer at concentrations of between approximately 0.01 wt. % to 5.0 wt %, preferably less than 1 wt.%.

In FIG. 2D excess dye-containing lens-grade polymer is removed using a lathe or other suitable device. Next, in FIG. 2E clear, lens-grade polymer, generally the same polymer used to form the lens in FIG. 2A, but not limited to that polymer, is used to seal the lens and isolate the dye-containing polymer portion from the rest of the lens. Finally, the lens is milled to form an IOL and the clear polymer portion of the IOL surface is shaped to a predetermined diopter power without disturbing, or exposing, the underlying dye-containing-polymer material.

Thus, as taught herein IOLs are provided having a visible-light selective transmissive region wherein the visible light-selective transmissive region is less than the entire IOL. In one embodiment of the present invention the visible light-selective transmissive region is located near the lens center and protects the retina from exposure to damaging blue light wavelengths. In this embodiment the maximum blue light blocking effect is present under bright light conditions when the pupil is constricted such that the entire pupil opening is covered by the IOLs visible-light selective transmissive region. As the pupil dilates in lower light conditions more ambient blue light is allowed to pass through the pupil and enter the eye thus providing the blue light's non-vision beneficial effects to the IOL recipient. Moreover, the IOL recipient is generally not exposed to the visible light absorbing compound.

FIG. 2 depicts but one embodiment. Other embodiments of the present invention include IOLs having a structural polymer and a visible light selective-transmissive region disposed therein wherein the visible light selective-transmissive region is a light absorbing dye that forms a discrete region near said IOL's center. In this embodiment the light absorbing dye forms a gradient within said discrete region, the gradient having a highest concentration of light absorbing dye in the discrete region's center and a lowest dye concentration at the discrete region's border.

In another embodiment the IOL has an outer perimeter defining the IOLs edge, an anterior surface, a posterior surface and a visible light absorbing region defined between the anterior surface, said posterior surface and said outer perimeter wherein the visible light absorbing region comprises a dye, said dye not extending to said IOL's edge. In another embodiment the dye does not extend into said anterior surface or said posterior surface of said IOL. In still another embodiment the dye does not contact an anatomical structure or physiological fluid of a recipient's eye.

Figure 3B:
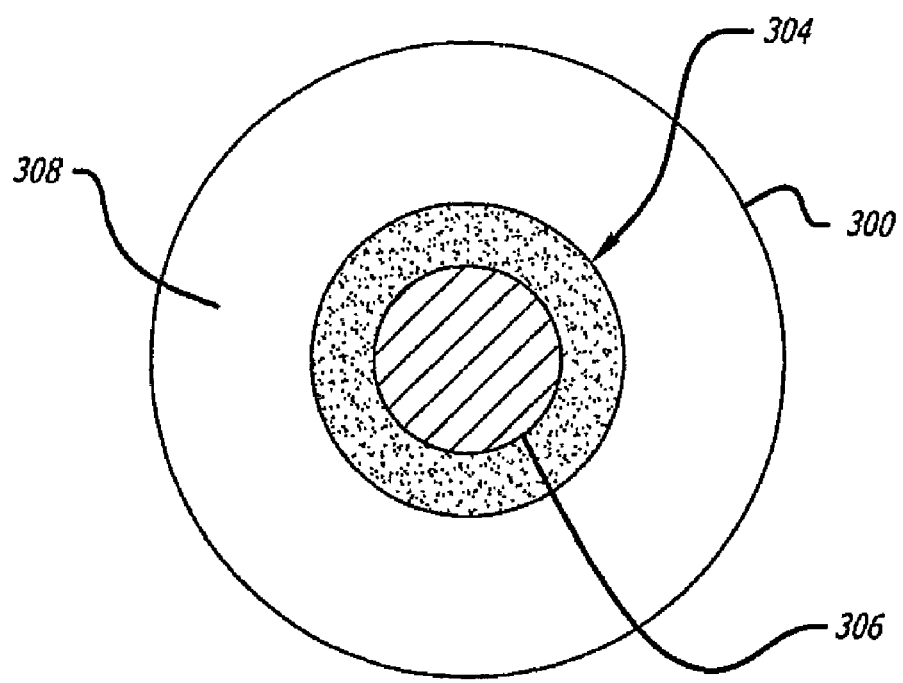
FIG. 3B depicts a multi-focal IOL made in accordance with the teachings of the present invention having an inner near vision correction zone and an outer far vision annular zone. Both the distance correction inner zone and the near correction outer annular zone are depicted having visible light-selective-transmissive regions.

FIG. 3B depict another embodiment of the present invention. One of the most common complaints or complications with multifocal IOL's is the observation of halos in low light when exposed to a bright light source. The halos are due to different focal images produced by the multifocal lens. Use of a blue blocker in one of the multifocal zones could reduce the amount of light transmitted through this zone and hence reduce halos produced by this zone.

In one embodiment, a refractive multifocal lens, the first zone/center portion 306 of the lens 300 is 2.1 mm in diameter and designed for distance correction. The second zone 304 is annular in shape, ranges between 2.1 mm and 3.4 mm in diameter, and is designed for near vision correction. Both the first and second zone contain a blue blocker, provide retinal protection in bright light, and provide distance and near vision. The third zone 308 is annular in shape, between 3.4 and 5.0 mm in diameter, designed for distance correction, does not contain a blue blocker, or contains a blue blocker at much lower effective concentrations that than the first and second zones, and allows more light to enter the eye under low or mid-light conditions than the same lens made entirely of blue blocking material. Because the second zone (2.1 to 3.4 mm) contains a blue blocker, the relative intensity of this light hitting the retina under low or mid-light conditions is less and halos produced by this lens also may be less.

The second example is comparable to the first except the center portion of the lens 306 (up to 2.1 mm in diameter) does not contain a blue blocker. Use of a blue blocker portion of the lens that provides the add power 304 may allow more functionality and flexibility in the design of multifocal lenses. For example, the add power of the lenses may be optimized increased without a significant increase in halos. In addition, a larger portion or percentage of the lens may be used for near correction without necessarily producing more halos.

In summary, this invention allows for better retinal protection in bright conditions, less halos in low light conditions, and more flexibility in the designs of multifocal lenses with respect to the add power and increasing the percentage of light intended for near vision correction.

Finally, the present invention has been described in terms of using a dye to absorb, or block, specific wavelengths of light—blue-violet—from reaching the retina. However, the present invention also includes other means for blocking blue-violet light from reaching the retina. In one embodiment, the visible light-selective-transmissive region is provided to the lens surface as a coating.

In another embodiment, diffractive patterns that defocus the blue-violet light are provided. Diffractive lenses consists of a series of radial rings or "zones" of decreasing width. The structure focuses light because rays incident on the outer zones of the lens are deviated more than rays incident on the center. Light of different wavelengths will be deviated by different amounts so different colors are focused at different distances behind the lens. The diffractive pattern may use this effect for monofocal lenses and multifocal lenses, and different regions of the lens may have a different amount of defocusing effect.

While this invention has been described with reference to preferred embodiments thereof, these are by way of illustration and not limitation. Variations and modifications thereon can be made by those skilled in the art without departing from the scope or spirit of the invention.

What is claimed is:

1. A method for making an intraocular lens (IOL) optic, the method comprising:
   a) forming a lens-grade polymer disc structure with a well centrally defined therein;
   b) filling said well with a visible light absorbing dye;
   c) covering said polymer structure and said well containing said visible light absorbing dye with a polymer to form a dye-containing polymer structure; and
   d) milling said dye-containing polymer structure to form said intraocular lens optic,
   wherein said visible light absorbing dye is entirely enclosed by the polymer disc structure as a discrete central region within the optic such that the visible light absorbing dye does not contact either the eye's anatomical structures or physiological fluids, wherein the visible light absorbing dve absorbs visible light between the wavelengths of 400λ and 550λ, wherein the visible light absorbing dye is a methine class dye having a concentration which is constant regardless of diopter strength, and wherein the discrete central region has a diameter less than about 4.5 mm.

2. The method according to claim 1 wherein said polymer is selected from the group consisting of acrylates, silicones, hydrogels, and acrylic-silicone hybrids.

3. A method for forming an intraocular lens (IOL) optic, the method comprising:
- a) forming a lens-grade polymer disc structure using a first polymer; said polymer structure having a top surface;
- b) forming a well centrally defined in said top surface of said polymer structure;
- c) filling said well with a visible light absorbing dye;
- d) covering said polymer structure top surface and said visible light absorbing dye containing well with said first polymer forming a dye-containing polymer structure; and
- e) shaping said dye-containing polymer structure into said intraocular lens optic, wherein said visible light absorbing dye is entirely enclosed by the polymer disc structure as a discrete central region within the optic such that the visible light absorbing dye does not contact either the eye's anatomical structures or physiological fluids, wherein the visible light absorbing dve absorbs visible light between the wavelengths of 400λ and 550λ, wherein the visible light absorbing dye is a methine class dye having a concentration which is constant regardless of diopter strength, and wherein the discrete central region has a diameter less than about 4.5 mm.

* * * * *